United States Patent [19]

Kamiya et al.

[11] 4,361,028
[45] Nov. 30, 1982

[54] SYSTEM FOR MEASURING PARTICULATE DISCHARGE FROM VEHICULAR INTERNAL COMBUSTION ENGINE

[75] Inventors: Sigeru Kamiya, Chiryu; Junji Wakayama, Okazaki; Nobutoshi Hayashi, Nishio; Hiroshi Noguchi, Gotenba; Kenichi Uchida; Nobuhisa Mori, both of Susono, all of Japan

[73] Assignees: Nippon Soken, Inc., Nishio; Toyota Jidosha Kogyo Kabushiki Kaisha, Toyota, both of Japan

[21] Appl. No.: 235,987

[22] Filed: Feb. 19, 1981

[30] Foreign Application Priority Data

Feb. 22, 1980 [JP] Japan .................................. 55-21769

[51] Int. Cl.³ .......................................... G01N 15/00
[52] U.S. Cl. ..................................................... 73/28
[58] Field of Search .................. 73/28, 863.22, 863.23, 73/23; 55/270

[56] References Cited

U.S. PATENT DOCUMENTS 3,817,100 6/1974 Anderson et al. ............... 73/863.23
3,903,727 9/1975 Sweet ....................................... 73/28
3,986,386 10/1976 Beltzer et al. ............................ 73/28

FOREIGN PATENT DOCUMENTS 381971 8/1973 U.S.S.R. .................................. 73/28

Primary Examiner—Stephen A. Kreitman
Attorney, Agent, or Firm—Cushman, Darby & Cushman

[57] ABSTRACT

A system for measuring particulate discharge from a vehicular internal combustion engine has a dilution tunnel into which exhaust gases are introduced and mixed with and diluted by clean air. A part of the diluted gases is introduced through a sampling probe into a sampled gas line in which a filter is provided to collect particulates contained in the sampled gases. A differential pressure transducer is provided to detect the pressure drop across the filter and convert the detected pressure drop into an electric signal which is fed into an operator which is operative to compute the quantity of particulate content of the engine exhaust gases on the basis of the time differential of the electric signal from the differential pressure transducer.

3 Claims, 6 Drawing Figures

SYSTEM FOR MEASURING PARTICULATE DISCHARGE FROM VEHICULAR INTERNAL COMBUSTION ENGINE

BACKGROUND OF THE INVENTION

1. Field of the Invention

The present invention relates to a system for measuring the quantity of particulates contained in exhaust gases from an internal combustion engine mounted on a vehicle.

2. Description of the Prior Art

There is a tendency that vehicles equipped with Diesel engines have been increased in number because of better fuel consumption rate of this type of engines compared with gasoline engines. However, Diesel engines discharge larger amounts of particulates than those discharged by gasoline engines. The particulate discharge is seriously considered from the view point of environmental pollution. For this reason, the governments of some countries, such as U.S.A., are inclined to provide some severe regulation concerning the quantities of particulates discharged from Diesel engines. Under the circumstance, it is particularly important to know the particulate discharge characteristics or vehicles and, more particularly, the particulate discharge of each vehicle which varies from a moment to the next moment. The prior art particulate discharge measuring system, however, is inoperable to continuously measure the particulate discharge.

SUMMARY OF THE INVENTION

It is an object of the present invention to provide an improved particulate discharge measuring system operative to continuously measure the particulate discharge from a vehicle.

It is another object of the present invention to make it possible, by adding simple means to the prior art measuring system, to measure the quantity of particulates discharged from a vehicle during a very minute period of time during operation of the vehicle.

According to the present invention, there is provided an improved system for measuring the quantity of particulates contained in exhaust gases from an internal combustion engine of a vehicle, comprising a mixing section in which the engine exhaust gases are mixed with and diluted by a large amount of clean air, a blower means for sucking the engine exhaust gases and the clean air into said mixing section and discharging the mixed and diluted gases therefrom, gas sampling means for sampling a part of the flow of the diluted gases, said gas sampling means including a sampled gas line for the flow of the sampled gases, a sampling probe through which the sampled gases flow into said sampled gas line, a sampling pump disposed in said sampled gas line for sucking the sampled gases into said line and discharging the sampled gases therefrom, filter means disposed in said line between said probe and said sampling pump for collecting the particulates contained in the sampled gases, the improvement which comprises means for detecting the pressure drop across said particulate collecting filter means and converting the detected pressure drop into an electric signal, and a particulate discharge operation means operative to compute the quantity of particulate content of the engine exhaust gases on the basis of the time differential of said electric signal.

The particulate measuring system of the present invention may preferably be provided with means for measuring the flow rate of the sampled gases through the sampled gas line and converting the measured flow rate into a second electric signal to be fed into the particulate discharge operation means as a factor of the equation which is operated by the operation means. In addition, the system of the invention may also be provided with mean for detecting the temperature of the sampled gases to provide for the correction of the filter pressure drop in accordance with the detected temperature of the sampled gases.

The above and other objects, features and advantages of the invention will be made more apparent by the following description with reference to the accompanying drawings.

DESCRIPTION OF PREFERRED EMBODIMENTS

Before describing embodiments of the present invention, the prior art will be described in more detail than in the above prior art description.

In general, the principal components of the particulate material contained in exhaust gases from Diesel engines are carbon particles in which red-burned hydrocarbon, organic combustion product compounds, sulphate and so on are absorbed in the peripheries of the particles. As such, the particulates contained in the engine exhaust gases include the thermally unstable organic compounds. In order that the discharge of the particulates may be measured in such a manner that the particulates when subjected to the measurement are nearly in the state which they have when they are discharged into the atmosphere and such that the condensation of the water contained in the sampled amount of exhaust gases is avoided, the measurement of the particulate discharge has been conducted such that exhaust gases are mixed with and diluted by a large amount of cleaned air and, thereafter, a part of the diluted exhaust gases is sampled and passed through a filter to separate the gases from the particulates which are then weighed to decide the particulate discharge. This method of particulate discharge measurement is called as dilution sampling method.

Figure 1:
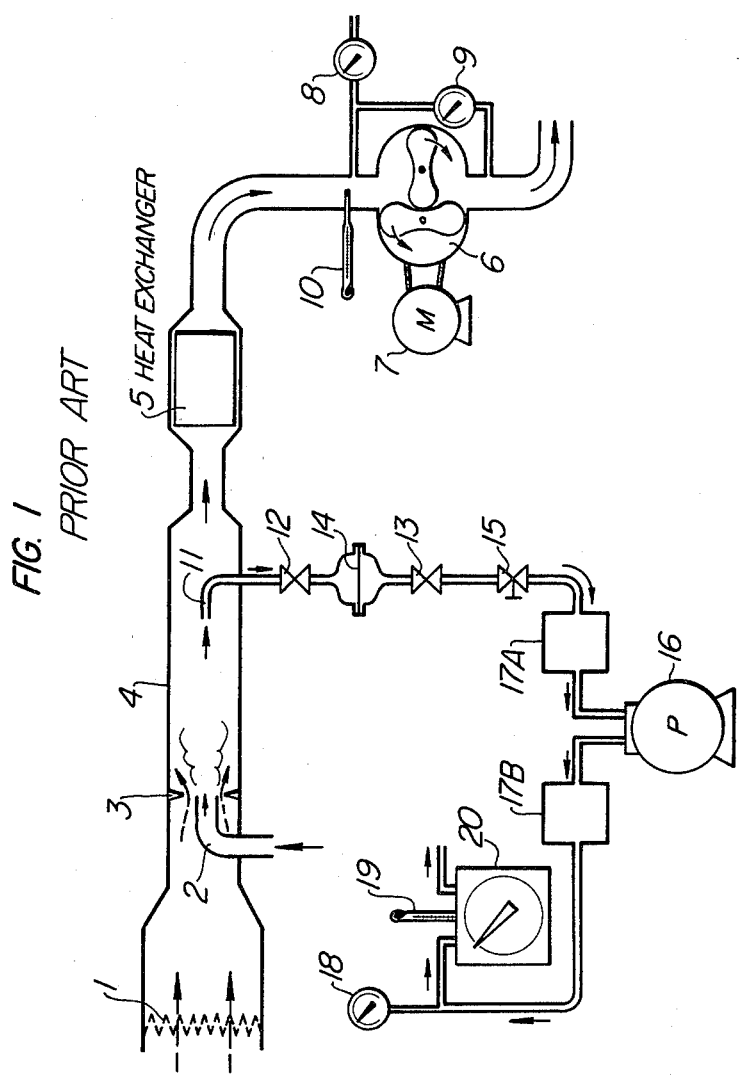
FIG. 1 is a diagrammatic illustration of the prior art particulate discharge measuring system.

The particulate discharge measuring system conventionally used will be described hereunder with reference to FIG. 1. The section of the system comprising the parts designated by reference numerals 1 through 4 constitutes a mixing section. The part 4 is called as a dilution tunnel and operative to uniformly mix vehicular engine exhaust gases supplied through an exhaust gas supply conduit 2 with diluting air which has been cleaned by an air filter 1. Reference numeral 3 designates an orifice which is operative to cause a turbulence in the diluted gases to an appropriate extent so as to facilitate uniform mixture of the exhaust gases and the air. Reference numeral 6 denotes a blower, which is in the form of a Root's blower, for introducing or sucking the diluted gases into the system and discharging the gases out of the system. The blower is driven by a motor 7. In order that the flow rate of the diluted gases is accurately metered, pressure gauges 8 and 9 are provided to measure the pressure of the gases at the inlet of the Root's blower and the pressure difference across the Root's blower and, in addition, a thermometer 10 is provided to measure the temperature of the gases at the inlet of the Root's blower. A heat exchanger 5 is provided to insure that the diluted gases flow into the blower 6 at a constant temperature.

A part of the diluted gases which have been uniformly mixed in the dilution tunnel 4 is guided out of the tunnel 4 by a sampling probe 11 and caused to flow through a particulate collection filter 14 (which is simply called as "filter" hereinafter) so that the particulates contained in the gases are separated therefrom and collected on the filter 14. Reference numeral 20 designates a gas meter operative to measure the flow of the sampled amount of gases, reference numeral 16 designates a suction pump operative to suck the sampled gased from the dilution tunnel 4 and discharge the sampled gases out of the system, and reference numeral 15 designates a needle valve for adjusting the flow rate of sampled gases. Reference numerals 12 and 13 denote valves which are opened only during the sampling operation of the system so that the filter 14 is prevented from being subjected to unnecessary pressure variation during the time when the system is not operated to conduct sampling. Reference numerals 17A and 17B designate buffer tanks operative to absorb the pulsation caused by the suction pump 16. Numerals 18 and 19 respectively denote a manometer for measuring the pressure of the gases at the inlet of the gas meter 20 and a thermometer for measuring the gas temperature within the gas meter 20. These manometer and thermometer are provided to accurately measure the flow of the sampled gases.

The system described above starts its sampling operation when a vehicle equipped with an internal combustion engine to be tested is started to run according to predetermined modes of operation. The sampling operation is discontinued when the vehicle is stopped. The weight of the particulates collected by the filter 14 during the operation of the vehicle is decided by the difference in weight of the filter before and after the particulates are collected. The amount of the particulates discharged from the engine of the vehicle is given by the following equation:

$$W = w \times \frac{QT + qT}{qT} \quad (1)$$

where W is the weight of the particulates discharged during the mode operation of the vehicle; w is the weight of the particulates collected on the filter; QT is the total quantity of the diluted gases sucked and discharged by the blower 6 during the sampling operation; and qT is the quantity of the sampled gases which has passed through the filter 14 during the sampling operation.

As will be apparent from the foregoing description, since the prior art particulate discharge measuring system is designed such that the filter 14 with collected particulates thereon is weighed after the mode operation of the vehicle to decide the amount or weight of the collected particulates, it is impossible to known the actual state or condition of particulate discharge which varies from moment to moment during the vehicle operation. The present invention aims at obtaining the quantity of discharged particulate by measuring the air-flow resistance of the particulate collection filter to thereby make it possible to measure the particulate discharge during mode operations of vehicles.

Figure 2:
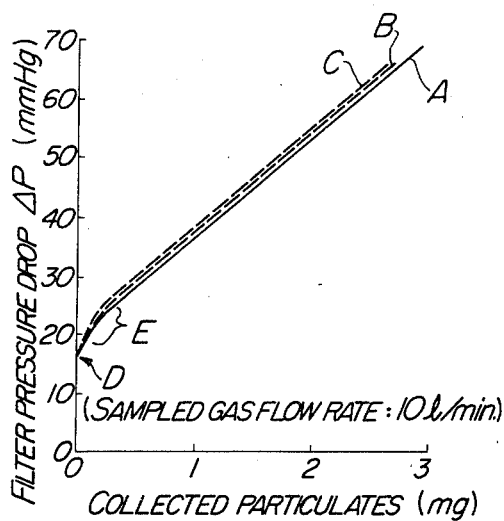
FIGS. 2 and 3 are graphs useful for the understanding of the operation of the particulate discharge measuring system according to the present invention, wherein FIG. 2 graphically illustrates the relationship between the quantity of collected particulates relative to the filter pressure drop and FIG. 3 graphically illustrates the relationship between the sampled gas flow rate relative to the filter pressure drop.
Figure 3:
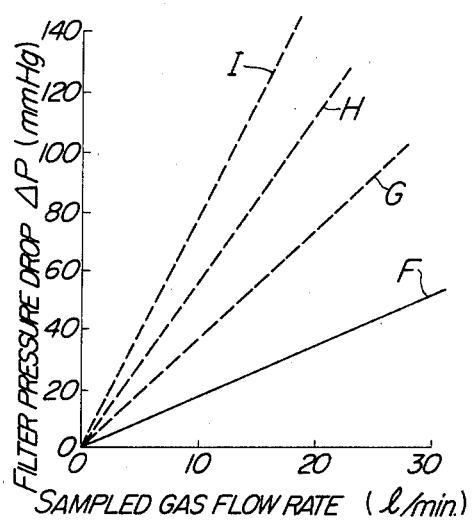

It can be easily presumed that the air-flow resistance of the filter would increase as the quantity of particulates deposited on the filter is increased. The present invention is not grounded unless the two factors are in quantitative relationship with each other. In addition, it was thought that deposits of particulates of the same weight would give different air-flow resistances if the particulates were of different properties and that particulates discharged from a Diesel engine would have different properties according to different engine operation conditions. Tests and researches have been conducted to ascertain the presumption and thought discussed above. FIGS. 2 and 3 graphically illustrate the results of the tests and experiments.

More specifically, FIG. 2 illustrates the relationship between the quantity of collected particulates and the pressure drop ΔP across the collection filter, as obtained through experiments. Lines A, B and C in FIG. 2 respectively illustrate the results of tests in which the engine operation conditions were 1,000 r.p.m. at light load, 2,000 r.p.m. at intermediate load and 3,000 r.p.m. at heavy load. The point at D represents the air-flow resistance of the filter it-self. It will be understood from the graphical illustration in FIG. 2 that the filter pressure drop ΔP is in close proportional relationship to the quantity of the collected particulates and is not influenced by different engine operation conditions. The present invention is based on this relationship between the quantity of the collected particulates and the filter pressure drop ΔP.

The lines A, B and C shown in FIG. 2 are not linear in the zone E. This is because the filter becomes clogged to a certain extent at the initial part of the particulate collecting operation. It will be seen in FIG. 2 that, after the deposit of the particulates on the filter exceeds a certain value, the deposit of particulates forms a layer and, thereafter, the relationship between the quantity of the collected particulates and the filter pressure drop becomes linear.

FIG. 2 shows the results of tests in each of which the sampled gas flow rate was constant (i.e., 10 l/min.). Actual particulate discharge measurement tests, however, are conducted at various sampled gas flow rates. In addition, it is thought that the sampled gas flow rate would be slightly changed during each test. Thus, the relationship between the filter pressure drop and the sampled gas flow rate must also be made clear. FIG. 3 graphically illustrates the results of tests conducted for this purpose. Line F in the drawing represents the filter pressure drop ΔP of a filter with no particulates collected thereon, whereas lines G, H and I show pressure drops of filters with 1 mg, 2 mg and 3 mg of particulates collected thereon, respectively. It will be seen in FIG. 3 that the filter pressure drops of respective tests are all in linear relationship to the sampled gas flow rates. This is because the particulates and the apertures of the filters are of very small diameters and, thus, the major parts of the air-flow resistance of the layer of the particulates on the filter and the air-flow resistance of the filter it-self are of the viscosity resistance of the fluid; namely, the flow of the collected gases through the filter and the layer of the collected particulates thereon is so-called "Darcy-flow".

The afore-discussed pressure drop characteristics of the particulate collection filter 14 can be utilized in the following manner to know the states of particulate discharge of an engine during a mode operation of a vehicle and, more particularly, the quantity of particulate discharge per very minute unit of time (per second, for example).

The quantity W' of particulates discharged per unit of time is given by:

$$W' = m \times (Q+q) \quad (2)$$

where m is the weight of the particulates contained in a unit volume of sampled gases (mg/m$^3$, for example); and q is the flow rate of the sampled gases (m$^3$/second, for example).

Of the factors m, Q and q included in the equation (2), the factor m, the weight of the particulates contained in a unit volume of sampled gases, could not be obtained by the conventional measuring system. However, the above-discussed pressure drop characteristic of the particulate collection filter 14 can be utilized to obtain the amount of m in the following manner: Since the pressure drop of the filter 14 is in proportion to the amount of the particulates collected on the filter and also to the sampled gas flow rate, the increment of filter pressure drop d ($\Delta$P) during a very minute period of time dt is given by $$d(\Delta P) = K \cdot m \cdot q \cdot dt \cdot q \quad (3)$$

where $\Delta$P is the filter pressure drop (kg/m$^2$, for example); K is a constant determined by the filter diameter etc.; and the factor m·q·dt is the weight of the particulates collected on the filter during the time period dt (mg, for example).

The equation (3) can be rewritten into equation (4) to obtain the factor m:

$$m = \frac{1}{K \cdot q^2} \cdot \frac{d(\Delta P)}{dt} \quad (4)$$

where K is the constant determined by the filter diameter etc.; and $(d(\Delta P))/(dt)$ is the time differential of the filter pressure drop. By utilizing the equation (4) to obtain the weight m of the particulates contained in a unit volume of sampled gases, it is possible to obtain from the equation (2) the particulate discharge during a very minute period of time. As the flow rate Q of the diluted gases and the flow rate q of the sampled gases are substantially constant during sampling and measurement, these factors may be regarded as constants.

The above description can be summarized as follows: By obtaining the time differential of the pressure drop of the filter 14 which is proportional to the amount of collected particulates and to the flow rate of sampled gases, it is possible to know the weight of the particulates contained in a unit volume of sampled gases and, thus, it is possible to know the rate of the particulate discharge during mode operation of the vehicle.

Figure 4:
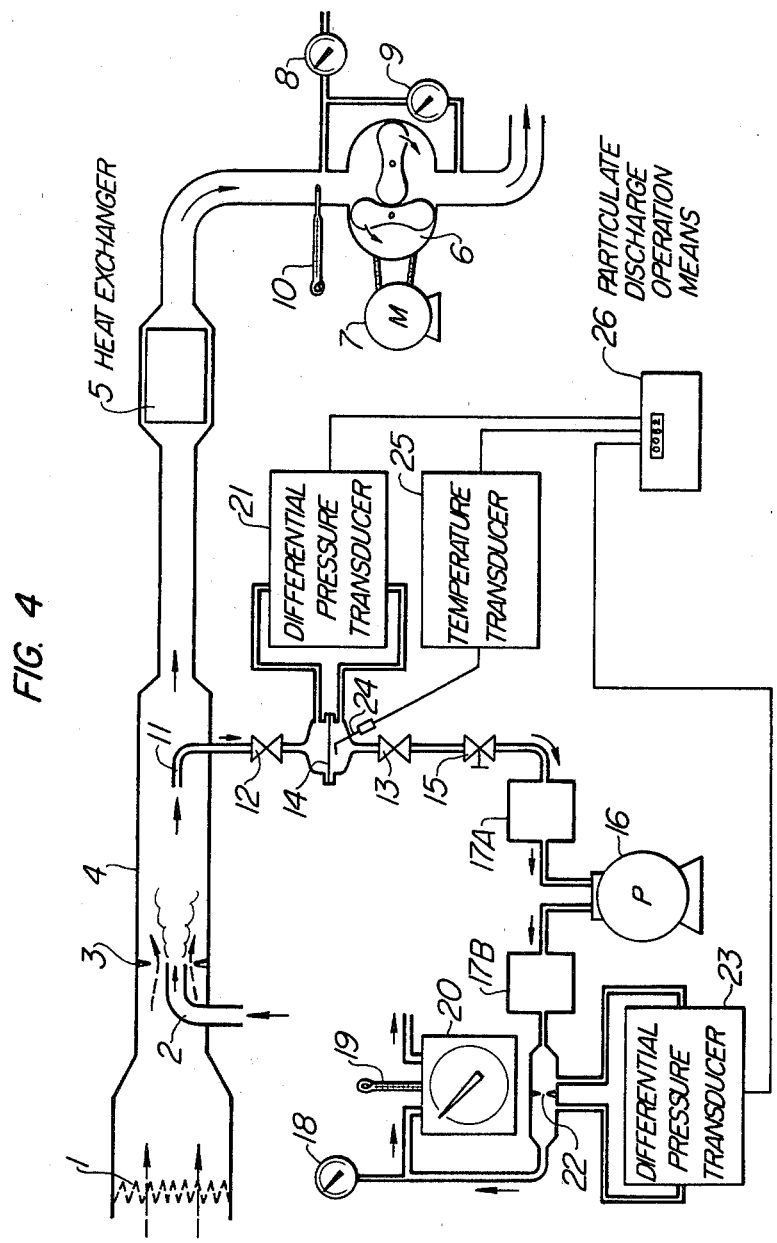
FIG. 4 is a view similar to FIG. 1 but diagrammatically illustrates an embodiment of the particulate discharge measuring system according to the present invention.

Now, an embodiment of the present invention will be described with reference to FIG. 4 wherein reference numerals 1 to 20 designate parts of the system similar or identical to those of the prior art system shown in FIG. 1. Reference numeral 21 designates a differential pressure transducer which constitutes a pressure drop detector and is operative to detect the difference between the pressure at points located upstream and downstream of the particulate collection filter 14; namely, the differential pressure transducer 21 is operative to measure the pressure drop across the filter 14 and emit an electric signal to a particulate discharge operation means 26. Reference numerals 22 and 23 designate an orifice and a differential pressure transducer, respectively. The combination of the transducer 23 and the orifice 22 constitutes means for measuring the flow rate of the sampled gases and is operative to convert the measured flow rate of sampled gases into an electric signal which is fed into the operation means 26. The particulate discharge operation means 26 functions to operate, according to the equation (4), the signal from the differential pressure transducer 21, which represents the filter pressure drop $\Delta$P, and the signal from the differential pressure transducer 23, which represents the flow rate q of the sampled gases. The output of the operation means 26 can be recorded or read on an indicator provided thereon. As the operation means 26 continuously provides an output which represents the weight m of the particulates contained in a unit volume of sampled gases, it is possible to continuously know the particulate discharge during vehicle operation.

The actual amount of the discharged particulates is equal to the weight m of the particulate in a unit volume of sampled gases multiplied by the sum of the flow rate Q of the diluted gases through the blower 6 and the flow rate q of the sampled gases. However, because the flow rates Q and q are substantially constant during measurement of particulate discharge, there is no need to subject these factors to the operation in the operating means 26.

The pressure drop across the filter is proportional to the flow rate of the sampled gases, as discussed above. Exactly speaking, moreover, the filter pressure drop is also proportional to the coefficient of viscosity of the sampled gases. The viscosity coefficient of the gas depends upon the temperature of the sampled gases. Thus, so as to conduct a highly accurate and precise measurement, it is advisable to detect or measure the temperature of the sampled gases to provide for the correction of the filter pressure drop in accordance with the detected gas temperature. For this purpose, a thermocouple 24 is disposed downstream of the particulate collection filter 14 so that an electric signal representing the detected temperature is fed through a temperature transducer 25 into the particulate discharge operation means 26. The temperature-based correction of the value m obtained by the operation is equal to about 8% for the gas temperature change of 20° C.

It is to be understood that the particulate discharge operation means 26 can be easily made on the basis of the conventional and well-known electric circuit technology.

Figure 5:
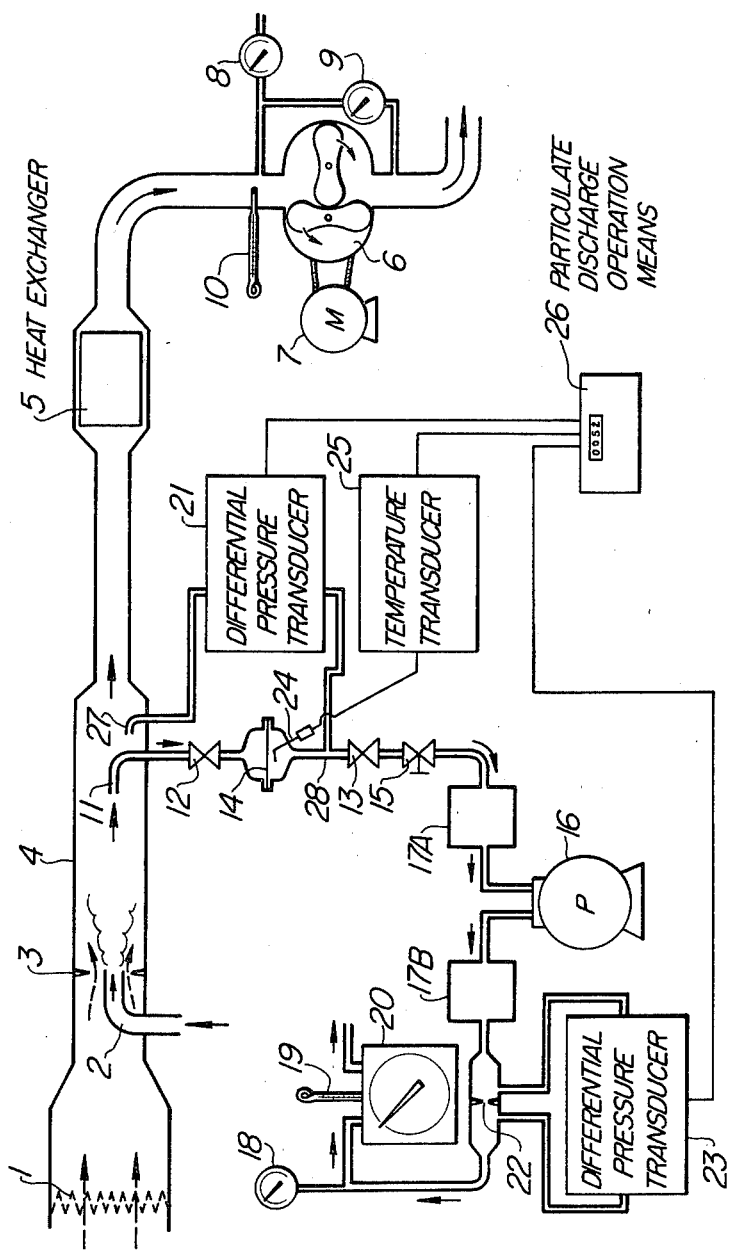
FIG. 5 is similar to FIG. 4 but diagrammatically illustrates another embodiment of the invention.

FIG. 5 illustrates another embodiment of the invention. In the preceding embodiment of the invention, the filter pressure drop is detected by measuring the pressures of the sampled gases at points adjacent to the filter 14. In the embodiment shown in FIG. 5, however, the gas pressure upstream of the filter 14 is detected at a point 27 located within the dilution tunnel 4, whereas the gas pressure downstream of the filter is detected at a point within a gas pipe 28 downstream of the filter 14. The modified embodiment provides an improvement in the operability of the system.

In the described embodiments of the present invention, the orifice 22 is utilized to provide for the measurement of the flow rate of the sampled gases and the result of the measurement is converted into an electric signal which is continuously fed into the particulate discharge operation means 26 for operation therein. However, the system of the invention may alternatively be designed such that the flow rate of the sampled gases is kept substantially constant, in which case the flow rate of the sampled gases may be regarded as a constant. In addition, the measurement of the flow rate of the sampled gases may be conducted not only by means of the orifice but also by means of laminar flow type flow meter, heat-quantity type flow meter or the like. Moreover, the operation of the equation (2) can be conducted by means of the operation means 26.

Figure 6:
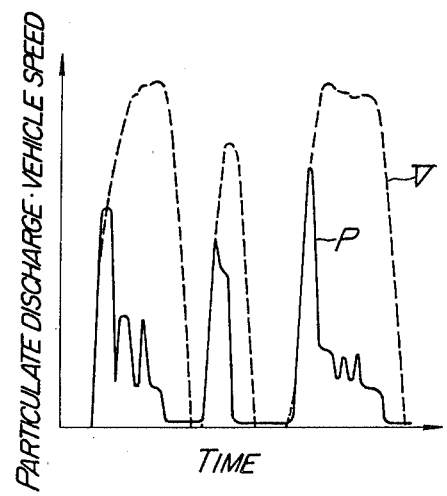
FIG. 6 is a graphical illustration of ever-varying particulate discharge from an internal combustion as measured by the system of the present invention.

FIG. 6 illustrates an example of a records of the measurements of the particulate discharge during vehicle operations as conducted by means of the system of the present invention, wherein curve P represents the particulate discharge while V represents the vehicle speed. It will be seen in the drawing that the particulate discharge is remarkably increased during acceleration operations of the vehicle.

It will be appreciated from the foregoing description that the prior art particulate discharge measuring system was not operable to measure the quantity of particulates discharged for a very minute period of time during vehicle operation, but the system of the present invention is advantageously operable to measure the quantity of the particulates discharged for a very minute period of time during vehicle operation to thereby insure that the particulate discharge characteristics of vehicles can easily be known. This is because the system of the present invention is designed to measure the pressure drop across the particulate collection filter and compute the quantity of particulates in the engine exhaust gases on the basis of time differential of the filter pressure drop.

What is claimed is:

1. In a system for measuring the quantity of particulates contained in exhaust gases from an internal combustion engine, comprising a mixing section in which the engine exhaust gases are mixed with and diluted by a large amount of clean air, a blower means for sucking the engine exhaust gases and the clean air into said mixing section and discharging the mixed and diluted gases therefrom, gas sampling means for sampling a part of the flow of the diluted gases, said gas sampling means including a sampled gas line for the flow of the sampled gases, a sampling probe through which the sampled gases flow into said sampled gas line, a sampling pump disposed in said sampled gas line for sucking the sampled gases into said line and discharging the sampled gases therefrom, filter means disposed in said line between said probe and said sampling pump for collecting the particulates contained in the sampled gases, the improvement which comprises means for detecting the pressure drop across said particulate collecting filter means and converting the detected pressure drop into an electric signal, and a particulate discharge operation means operative to compute the quantity of particulate content of the engine exhaust gases on the basis of the time differential of said electric signal.

2. The particulate measuring system as defined in claim 1, further including means for measuring the flow rate of the sampled gases through said line and converting the measured flow rate into a second electric signal, said second electric signal being also fed into said particulate discharge operation means as a factor of the equation operated by said operation means.

3. The particulate measuring system as defined in claim 1 or 2, further including means for detecting the temperature of the sampled gases to provide for the correction of the filter pressure drop in accordance with the detected temperature of the sampled gases.

* * * * *